(12) United States Patent
Suzuki et al.

(10) Patent No.: US 11,617,691 B2
(45) Date of Patent: Apr. 4, 2023

(54) ABSORBENT ARTICLE

(71) Applicant: Kao Corporation, Tokyo (JP)

(72) Inventors: Takeshi Suzuki, Sano (JP); Mina Tomita, Utsunomiya (JP); Ayako Makino, Utsunomiya (JP)

(73) Assignee: KAO CORPORATION, Tokyo (JP)

( * ) Notice: Subject to any disclaimer, the term of this patent is extended or adjusted under 35 U.S.C. 154(b) by 498 days.

(21) Appl. No.: 16/761,989

(22) PCT Filed: Nov. 16, 2018

(86) PCT No.: PCT/JP2018/042535
§ 371 (c)(1),
(2) Date: May 6, 2020

(87) PCT Pub. No.: WO2019/102948
PCT Pub. Date: May 31, 2019

(65) Prior Publication Data
US 2020/0315865 A1    Oct. 8, 2020

(30) Foreign Application Priority Data

Nov. 22, 2017  (JP) .............................. JP2017-224995

(51) Int. Cl.
*A61F 13/511* (2006.01)
*A61F 13/512* (2006.01)
(Continued)

(52) U.S. Cl.
CPC ........ *A61F 13/512* (2013.01); *A61F 13/5123* (2013.01); *A61F 13/51104* (2013.01);
(Continued)

(58) Field of Classification Search
CPC .............. A61F 13/511; A61F 13/51104; A61F 13/51108; A61F 13/5116; A61F 13/512;
(Continued)

(56) References Cited

U.S. PATENT DOCUMENTS

2005/0148970 A1    7/2005   Kudo et al.
2010/0249740 A1    9/2010   Miyamoto et al.
(Continued)

FOREIGN PATENT DOCUMENTS

CN    203447435 A    2/2014
CN    205411476 U    8/2016
(Continued)

OTHER PUBLICATIONS

International Search Report (PCT/ISA/210) issued in PCT/JP2018/042535, dated Jan. 22, 2019.
(Continued)

*Primary Examiner* — Michael A Tolin
(74) *Attorney, Agent, or Firm* — Birch, Stewart, Kolasch & Birch, LLP (57) ABSTRACT

Provided is a disposable diaper (1) which includes an absorbent member (4) and a topsheet (2). The topsheet (2) includes a first sheet (20) and a second sheet (21). Both sheets (20) and (21) are partially joined to form a plurality of joined regions (22), and the first sheet (20) has a plurality of projections (23) which protrude from the second sheet (21) toward the wearer's skin side at a portion other than the joined regions (22). The projections (23) include first projections (23A) and second projections (23B) and, when the topsheet (2) is viewed in a plan view, a second projection region (23R) is formed which includes the second projections (23B) surrounded by the plurality of first projections (23A). When the topsheet (2) is viewed in a plan view, the joined regions (22) include an inner joined region (22A1) in the second projection region (23R).

16 Claims, 5 Drawing Sheets

(51) Int. Cl.
  *A61F 13/539* (2006.01)
  *B32B 37/12* (2006.01)
  *A61F 13/15* (2006.01)

(52) U.S. Cl.
  CPC ........ *A61F 13/539* (2013.01); *B32B 37/1292* (2013.01); *A61F 2013/15886* (2013.01); *A61F 2013/51178* (2013.01); *A61F 2013/51182* (2013.01); *A61F 2013/53908* (2013.01)

(58) Field of Classification Search
  CPC .............. A61F 13/5123; A61F 13/5126; A61F 13/539; A61F 2013/15861; A61F 2013/15869; A61F 2013/15878; A61F 2013/15886; A61F 2013/51178; A61F 2013/51182; A61F 2013/53908; A61F 2013/53925; A61F 2013/5395; A61F 2013/53958; B32B 37/0084; B32B 37/1207; B32B 37/1292; B32B 2037/1215
  See application file for complete search history.

(56) References Cited

U.S. PATENT DOCUMENTS

| | | |
|---|---|---|
| 2013/0158497 A1 | 6/2013 | Yamaguchi et al. |
| 2016/0074240 A1 | 3/2016 | Rosati et al. |
| 2016/0220421 A1 | 8/2016 | Kuramochi |
| 2017/0105888 A1 | 4/2017 | Kimura et al. |
| 2017/0312144 A1 | 11/2017 | Moritani |

FOREIGN PATENT DOCUMENTS

| | | | |
|---|---|---|---|
| CN | 205586162 U | | 9/2016 |
| CN | 106163472 A | | 11/2016 |
| CN | 107072831 A | | 8/2017 |
| CN | 107106363 A | | 8/2017 |
| CN | 107106364 A | | 8/2017 |
| EP | 2 656 826 A1 | | 10/2013 |
| GB | 2559705 A | | 8/2018 |
| JP | 2004-121701 A | | 4/2004 |
| JP | 2009-160035 A | | 7/2009 |
| JP | 2011-15707 A | | 1/2011 |
| JP | 2016-8367 A | | 1/2016 |
| JP | 2016-96926 A | | 5/2016 |
| JP | 2016-168299 A | | 9/2016 |
| JP | 2016-209535 A | | 12/2016 |
| JP | 2017-86706 A | | 5/2017 |
| JP | 2017-93732 A | | 6/2017 |
| JP | 2017-99593 A | | 6/2017 |
| JP | 2017099593 A | * | 6/2017 |
| JP | 2017-153915 A | | 9/2017 |
| JP | 2017153915 A | * | 9/2017 |
| RU | 2405517 C2 | | 8/2010 |
| TW | 201540274 A | | 11/2015 |
| WO | WO 2012/014957 A1 | | 2/2012 |
| WO | WO 2012/086487 A1 | | 6/2012 |
| WO | WO 2015/045842 A1 | | 4/2015 |
| WO | WO 2016/098848 A1 | | 6/2016 |
| WO | WO 2017/086076 A1 | | 5/2017 |

OTHER PUBLICATIONS

International Search Report for International Application No. PCT/JP2018/037974, dated Dec. 25, 2018, with an English translation.

* cited by examiner

ABSORBENT ARTICLE

TECHNICAL FIELD

The present invention relates to an absorbent article, such as a disposable diaper and a sanitary napkin.

BACKGROUND ART

Conventionally, as a topsheet for an absorbent article, such as a disposable diaper and a sanitary napkin, a topsheet is known where a skin-facing surface which is directed to the wearers skin side is formed into an uneven shape by performing pressing treatment, such as embossing treatment. For example, Patent Literature 1 discloses a topsheet which includes a plurality of projections of two sizes, that is large projections and small projections, on the skin-facing surface side, the large projections and the small projections being surrounded by a plurality of fusion bonded embosses, and having a three dimensional dome structure. According to the topsheet disclosed in Patent Literature 1, the large projections are arranged to surround the entire circumference of the small projections, thus causing a region including the small projections to function as a temporal storage portion for a body fluid. Accordingly, the body fluid discharged by a wearer does not easily adhere to the wearer's skin so that dryness is enhanced.

CITATION LIST

Patent Literature

Patent Literature 1: Japanese Patent Laid-Open No. 2011-15707

SUMMARY OF INVENTION

The present invention is directed to an absorbent article including: an absorbent member; and a topsheet disposed on a skin-facing surface side of the absorbent member, the absorbent article having a longitudinal direction, which corresponds to a front-rear direction of a wearer, and a lateral direction orthogonal to the longitudinal direction. The topsheet includes a layered body formed of a first sheet, disposed on the skin-facing surface side, and a second sheet, disposed on a non-skin-facing surface side, the first sheet and the second sheet of the layered body are partially joined to form a plurality of joined regions, and the first sheet has a plurality of projections, which protrude from the second sheet toward a wearer's skin side, at a portion other than the joined regions. The projections include a first projection and a second projection, and a height of the first projection is larger than a height of the second projection. When the topsheet is viewed in a plan view, a second projection region which includes the second projection surrounded by a plurality of the first projections is formed. When the topsheet is viewed in a plan view, the joined regions include an inner joined region in the second projection region.

DESCRIPTION OF EMBODIMENTS

However, the mere formation of the storage portion by surrounding the entire circumferences of the small projections by the large projections may cause the following problem. When a large amount of body fluid is discharged by a wearer, and exceeds the capacity of the storage portion, the body fluid may overflow from the storage portion, and adheres to the wearer's skin, thus causing stickiness and sweating.

In view of the above, the present invention relates to an absorbent article where, even in the case where a large amount of body fluid is discharged, a body fluid is smoothly transferred from a topsheet to an absorbent member so that dryness is enhanced by reducing stickiness and sweating.

Figure 1:
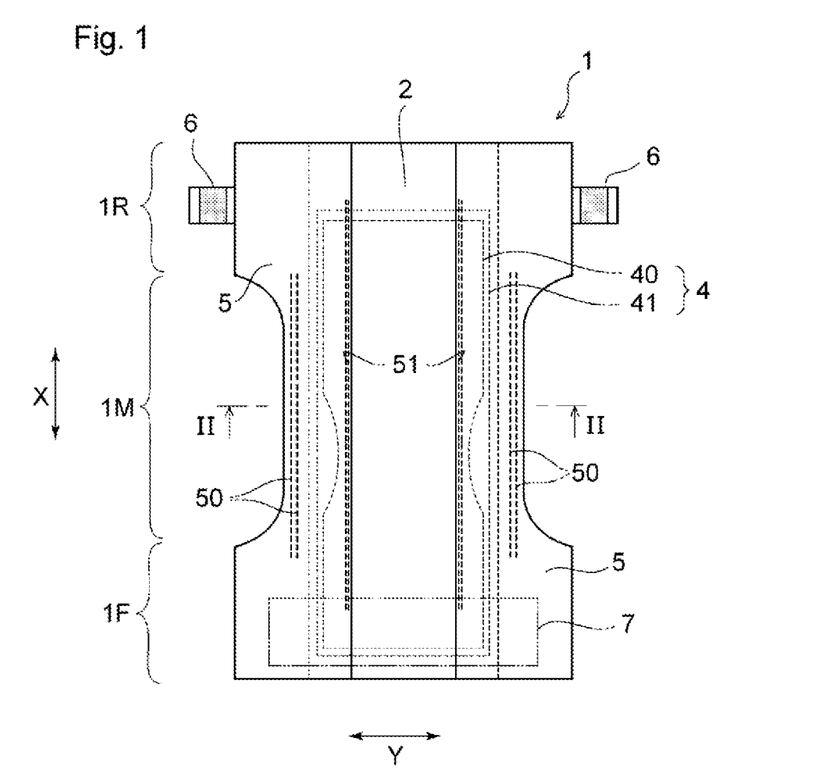
FIG. 1 is a plan view schematically showing a skin-facing surface, that is, the topsheet side of a disposable diaper which is one embodiment of an absorbent article of the present invention, and is also a plan view in a flat-out state where elastic members of respective portions are stretched to be expanded in a planar shape.
Figure 2:
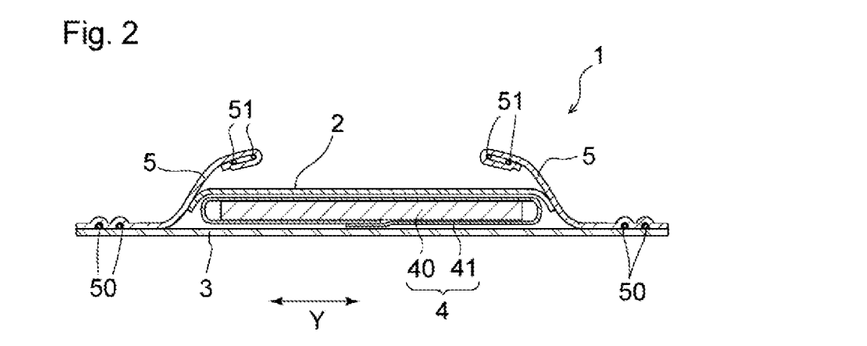
FIG. 2 is a transverse cross-sectional view schematically showing a cross section taken along a line II-II in FIG. 1.

Hereinafter, an absorbent article of the present invention will be described with reference to drawings based on a preferred embodiment. FIG. 1 and FIG. 2 show a disposable diaper 1 which is one embodiment of the absorbent article of the present invention. The diaper 1 includes a front portion 1F disposed on the front side of a wearer during wear, a rear portion 1R disposed on the rear side, and a crotch portion 1M positioned between the front portion 1F and the rear portion 1R. Further, the diaper 1 has a longitudinal direction X which extends from the front portion 1F to the rear portion 1R via the crotch portion 1M, and which corresponds to the front-rear direction of the wearer, and a lateral direction Y which is orthogonal to the longitudinal direction X. As described above, the front-rear direction of the wearer means a direction which extends from the front portion 1F to the rear portion 1R via the crotch portion 1M. The crotch portion 1M includes a discharging member facing portion which is disposed to oppose a discharging member, such as the penis of the wearer, during wear of the diaper 1. The discharging member facing portion is usually positioned at the center portion of the diaper 1 in the longitudinal direction X or in the vicinity of the center portion.

As shown in FIG. 1 and FIG. 2, the diaper 1 includes an absorbent member 4, and a liquid permeable topsheet 2 which is disposed on the skin-facing surface side of the absorbent member 4, and which may come into contact with the wearer's skin during wear. The diaper 1 also includes a liquid impermeable or water-repellent backsheet 3 disposed on the non-skin-facing surface side of the absorbent member 4. As shown in FIG. 1, as viewed in a plan view, the diaper 1 has an hourglass shape where the center portion of the diaper 1 in the longitudinal direction X which is positioned at the crotch portion 1M narrows inward, and the diaper 1 extends in one direction, that is, in the longitudinal direction X, the hourglass shape being oblong in the longitudinal direction. Each of the topsheet 2 and the backsheet 3 has a larger size than the absorbent member 4 disposed between both sheets 2 and 3. The topsheet 2 will be described later in detail. The backsheet 3 has a larger size than the topsheet 2, and extends outward from the peripheral edge of the absorbent member 4 and, as shown in FIG. 1, forms the outer shape of the diaper 1 in its flat-out and uncontracted state. For the backsheet 3, any of various sheets which are conventionally used for an absorbent article of this type may be used without any limitation, for example, a resin film, and a laminate of the resin film and a nonwoven fabric may be used.

In this description, the term "skin-facing surface" means a surface of the absorbent article or a constituent component (for example, the topsheet 2) of the absorbent article, the surface being directed toward the wearer's skin side during wear of the absorbent article. That is, the term "skin-facing surface" means the side relatively close to the wearer's skin. The term "non-skin-facing surface" means a surface of the absorbent article or the constituent component of the absorbent article, the surface being directed toward the side (clothes side) opposite to the skin side during wear of the absorbent article. That is, the term "non-skin-facing surface" means the side relatively far from the wearer's skin. The term "during wear" in this description means a state where a normal appropriate wearing position, that is, a right wearing position of the absorbent article is maintained, and a state where the absorbent article is displaced from the wearing position is not included.

As shown in FIG. 1, the absorbent member 4 has a shape oblong in the longitudinal direction X as viewed in a plan view, and the absorbent member 4 extends across a range from the front portion 1F to the rear portion 1R. The absorbent member 4 includes a liquid-retentive absorbent core 40 which includes an absorbent material, and a core-wrap sheet 41 which covers the skin-facing surface and the non-skin-facing surface of the absorbent core 40. The absorbent core 40 and the core-wrap sheet 41 are joined by a known joining means, such as a hot-melt-type adhesive.

The absorbent core 40 has a single layer structure. As shown in FIG. 1, as viewed in a plan view, the absorbent core 40 has an hourglass shape where the center portion of the absorbent core 40 in the longitudinal direction, that is, in the longitudinal direction X, is narrowed inward. The absorbent core 40 is formed by fiber stacking materials for forming a core, the material including an absorbent material. As the absorbent material, any material which is usually used as a material for forming an absorbent core of this type may be used without any limitation. The absorbent material may be wood pulp, a hydrophilicity fiber, such as a synthetic fiber on which treatment is performed using a hydrophilizing agent, or water-absorbing polymer particles, for example. That is, the absorbent core 40 may be formed of a fiber stacking body of the hydrophilicity fiber, or the fiber stacking body which is caused to carry the water-absorbing polymer particles.

For the core-wrap sheet 41, a water-permeable sheet material may be used so that a paper, a nonwoven fabric or the like may be used, for example. In the diaper 1 of this embodiment, the core-wrap sheet 41 is single continuous core-wrap sheet 41 having a width two times or more and three times or less greater than the length of the absorbent core 40 in the lateral direction Y. As shown in FIG. 2, this single core-wrap sheet 41 covers the entire skin-facing surface of the absorbent core 40, and extends outward in the lateral direction Y from both lateral edges of the absorbent core 40, both lateral edges extending along the longitudinal direction X. Extension portions of the core-wrap sheet 41 are caused to wrap the lower side of the absorbent core 40, thus covering the entire non-skin-facing surface of the absorbent core 40. The mode of the core-wrap sheet 41 is not limited to such a configuration. For example, the core-wrap sheet 41 may be configured such that the core-wrap sheet 41 includes a skin-side core-wrap sheet which covers the skin-facing surface of the absorbent core 40, and a non-skin-side core-wrap sheet which covers the non-skin-facing surface of the absorbent core 40, and both sheets are formed of separated sheets.

Further, side sheets 5 are respectively disposed on both lateral sides of the diaper 1 on the topsheet 2 side, the lateral sides extending along the longitudinal direction X. Each side sheet 5 includes an inner lateral side edge portion extending along the longitudinal direction X and an outer lateral side edge portion positioned outward of the inner lateral side edge portion in the lateral direction Y, and extending along the longitudinal direction X. As shown in FIG. 1, as viewed in a plan view, the inner lateral side edge portions overlap with the absorbent member 4. As shown in FIG. 2, the outer lateral side edge portions extend outward in the lateral direction Y from the lateral edges of the absorbent member 4, the lateral edges extending along the longitudinal direction X, and the outer lateral side edge portions are joined to the backsheet 3. Between each side sheet 5 of a left/right leg portion, disposed around the leg of a wearer, and the backsheet 3, filamentous elastic members 50 are fixed in a state of being stretched along the longitudinal direction X. Accordingly, a pair of leg gathers is formed by contraction of the elastic members 50 at the leg portion during wear of the diaper 1. Further, a filamentous elastic member 51 is fixed to the inner lateral side edge portion of each side sheet 5 in a state of being stretched along the longitudinal direction X. Accordingly, by contraction of the elastic member 51, the inner lateral side edge portion side of the side sheet 5 stands upright during wear of the diaper 1 at least at the crotch portion 1M toward the wearer's skin side using the joined region, where the side sheet 5 is joined to the backsheet 3, as a starting point so that a leak-proof cuff is formed. This leak-proof cuff can prevent flowing out of a discharge liquid, such as urine, outward in the lateral direction Y, that is, this leak-proof cuff can prevent so-called side leakage. The topsheet 2, the backsheet 3, the absorbent member 4, the side sheet 5, and the elastic members 50 and 51 are joined with each other by a known joining means, such as a hot-melt-type adhesive.

The diaper 1 is a so-called open type disposable diaper. As shown in FIG. 1, a pair of fastening tapes 6 and 6 is provided to both lateral edge portions of the rear portion 1R of the diaper 1, the lateral edge portions extending along the longitudinal direction X. An attachment portion not shown in the drawing and formed of a male member of a mechanical surface fastener is attached to each fastening tape 6. Further, a target region 7 formed of a female member of the mechanical surface fastener is formed on the non-skin-facing surface of the front portion 1F of the diaper 1. The target region 7 is formed such that the female member of the mechanical surface fastener is fixed by joining to the non-skin-facing surface of the backsheet 3, which forms the non-skin-facing surface of the front portion 1F, by a known joining means, such as an adhesive or a heat seal, for example. The attachment portions of the fastening tapes 6 can be detachably attached to the target region 7.

Figure 3:
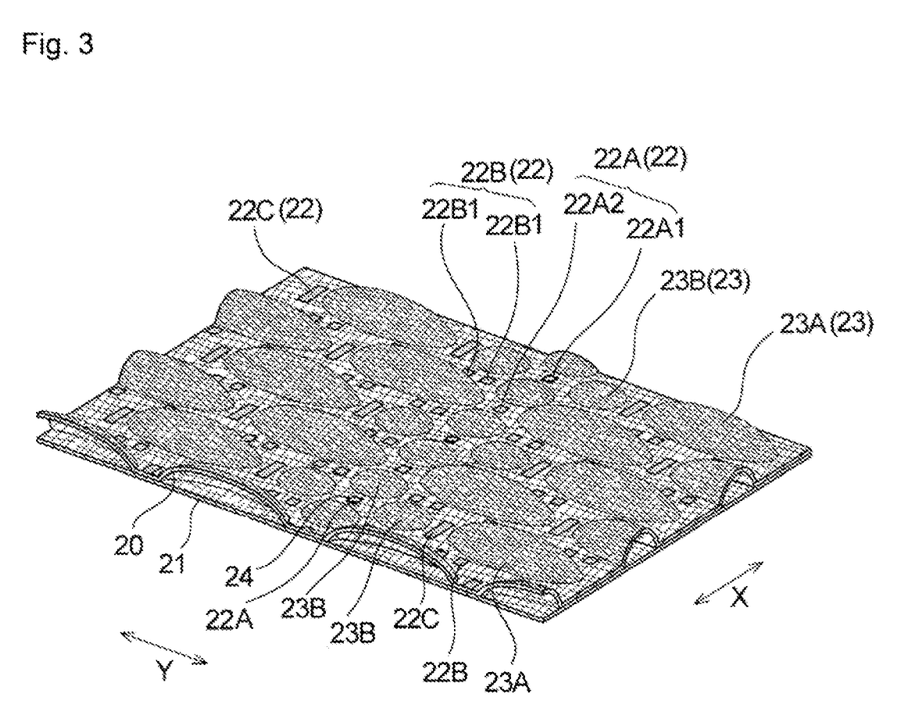
FIG. 3 is a perspective view schematically showing a portion on the skin-facing surface side of a topsheet provided to the diaper shown in FIG. 1.

Next, the topsheet 2 will be described with reference to FIG. 3. FIG. 3 shows a portion of the topsheet 2 in an enlarged manner. As shown in FIG. 3, the topsheet 2 is formed of a layered body formed of a first sheet 20 and a second sheet 21. The first sheet 20 is positioned on the body side of a wearer in a state where the wearer wears the diaper 1. The second sheet 21 is positioned on the absorbent member 4 side in a state where the wearer wears the diaper 1. The topsheet 2 includes a plurality of joined regions 22 where the first sheet 20 and the second sheet 21 are partially joined. The first sheet 20 protrudes in a direction away from the second sheet 21 at portions of the first sheet 20 other than the joined regions 22, the portions being surrounded by the joined regions 22 so that the portions form a plurality of projections 23 which protrude toward the wearer's skin side. In the topsheet 2, the second sheet 21 has a substantially flat shape, and unevenness having large undulations are formed on the first sheet 20, thus forming the plurality of projections 23.

The plurality of joined regions 22 may be formed by any of various means. In the case where the first sheet 20 and the second sheet 21 are made of a fusion bondable material, for example, fusion bonding using heat, ultrasonic, or high frequency may be used. Regardless of the material for forming the first sheet 20 and the second sheet 21, bonding by an adhesive may also be used. In the respective joined regions 22, the first sheet 20 and the second sheet 21 are pressed into an integral body and hence, the joined regions 22 of either one of the sheets 20 and 21 have a higher density than other portions of the sheets 20 and 21. It is preferable that both sheets 20 and 21 are fusion bonded by melting of a configuration resin for one of or both sheets and by subsequent solidification of the configuration resin.

It is sufficient for the plurality of projections 23 to be disposed at least at the crotch portion 1M. However, it is preferable that the plurality of projections 23 are disposed across a range from the crotch portion 1M to either one or both of the front portion 1F and the rear portion 1R. In the diaper 1, the plurality of projections 23 are disposed across the entire range from the front portion 1F to the rear portion 1R.

The topsheet 2, which is a layered body, has a first direction X and a second direction Y, which is orthogonal to the first direction X, in the plane of the sheet. In a state where the topsheet 2 is incorporated into the diaper 1, the first direction X is aligned with the longitudinal direction X, which is also the longitudinal direction of the diaper 1, and the second direction Y is aligned with the lateral direction Y, which is also the width direction of the diaper 1. In general, the first direction X of the topsheet 2 is aligned with a direction along which a raw fabric of the first sheet 20 and the second sheet 21 is repeated, and a conveying direction (MD) during manufacture of the topsheet 2 in many cases. Further, in general, in the case where the first sheet 20 and the second sheet 21 are formed of a nonwoven fabric, for example, the first direction X of the topsheet 2 is aligned with a primary orientation direction of fibers which form a nonwoven fabric in many cases.

Figure 4:
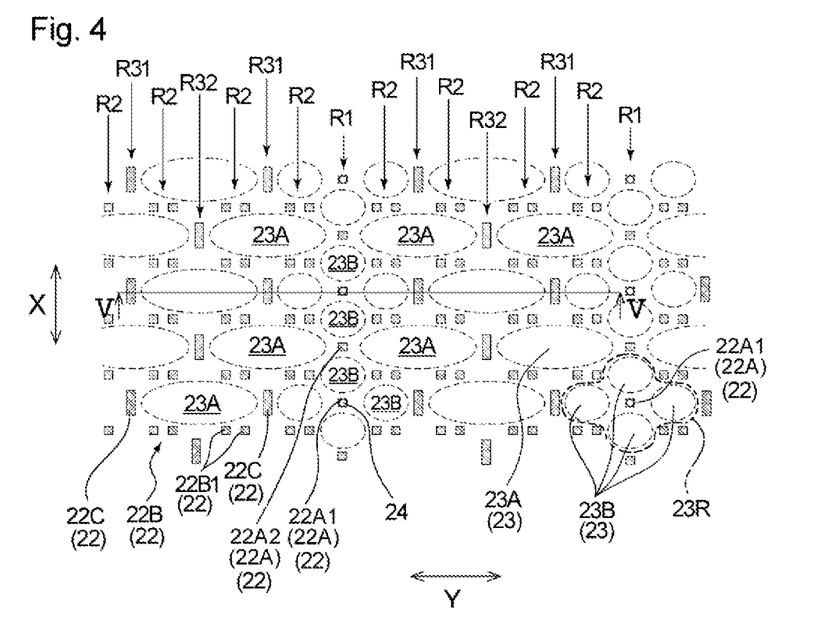
FIG. 4 is a plan view schematically showing a portion on the skin-facing surface side of the topsheet provided to the diaper shown in FIG. 1.
Figure 5:
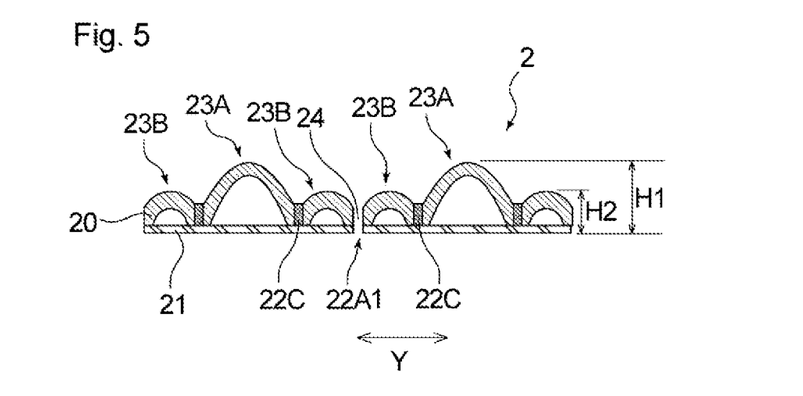
FIG. 5 is a transverse cross-sectional view schematically showing a cross section taken along a line V-V in FIG. 4.

Next, the plurality of joined regions 22 and the plurality of projections 23 of the topsheet 2 will be described with reference to FIG. 4 and FIG. 5 in addition to FIG. 3. FIG. 4 shows a plan view of a portion of the topsheet 2 shown in FIG. 3. FIG. 5 shows a cross-sectional view taken along a line V-V in FIG. 4.

As shown in FIG. 4, the topsheet 2 includes the plurality of joined regions 22 formed in a state of being regularly distributed in the plane direction of the topsheet 2. The topsheet 2 also includes the plurality of projections 23 at portions of the first sheet 20 other than the joined regions 22, the plurality of projections 23 protruding from the second sheet 21 to the wearer's skin side. The topsheet 2 includes, as the plurality of projections 23, a plurality of first projections 23A, and a plurality of second projections 23B smaller than the first projections 23A. The joined regions 22 include inner joined regions 22A1 each of which is disposed in a second projection region 23R which includes the second projections 23B surrounded by the plurality of first projections 23A when the topsheet 2 is viewed in a plan view. Hereinafter, the plurality of joined regions 22 and the plurality of projections 23 will be described in detail.

Specifically, the topsheet 2 includes, as the plurality of joined regions 22, a plurality of first joined regions 22A, which include the inner joined regions 22A1, a plurality of second joined regions 22B, and a plurality of third joined regions 22C. In these joined regions 22 (22A, 22B, and 22C), the first sheet 20 and the second sheet 21 are pressed into an integral body by embossing so that these joined regions 22 have a higher density than other portions where embossing is not performed. It is preferable that both sheets 20 and 21 are fusion bonded by melting of a configuration resin for one of or both sheets 20 and 21 and by subsequent solidification of the configuration resin.

The first joined regions 22A include the inner joined regions 22A1, each of which is disposed in the second projection region 23R, and outer joined regions 22A2 disposed outside the second projection region 23R. It is sufficient for each of the inner joined region 22A1 and the outer joined region 22A2 to be formed of one or more joined portions. In the diaper 1, each of the inner joined region 22A1 and the outer joined region 22A2 is formed of one joined portion having a square shape as viewed in a plan view. Each side of the inner joined region 22A1 and each side of the outer joined region 22A2 are aligned with the first direction X or the second direction Y. It is preferable that the inner joined region 22A1 has a through hole which penetrates the sheet. The diaper 1 has through holes 24 which penetrate the first sheet 20 and the second sheet 21. The outer joined region 22A2 may also have a through hole which penetrates the first sheet 20 and the second sheet 21. It is sufficient for each second joined region 22B to be formed of one or more joined portions. In the diaper 1, the second joined region 22B is formed of two second joined portions 22B1 and 22B1 formed into a square shape as viewed in a plan view. The outer shape of each of the second joined portions 22B1 and 22B1 as viewed in a plan view is formed into a square shape having a shape and size identical to the shape and size of the first joined region 22A as viewed in a plan view. Each side of the second joined portions 22B1 and 22B1 is aligned with the first direction X or the second direction Y. In this embodiment, "having a shape and size identical to the shape and size" means to have the same shape with a difference in size falling within the range of ±20% of the area. It is sufficient for each third joined region 22C to be formed of one or more joined portions. In the diaper 1, as shown in FIG. 4, the third joined region 22C is formed of one joined portion having a rectangular shape as viewed in a plan view. The longitudinal direction of the third joined region 22C is aligned with the first direction X, and the short direction of the third joined region 22C is aligned with the second direction Y.

As shown in FIG. 4, the plurality of first joined regions 22A form a first joined region row R1 where the first joined regions 22A are arranged in one row along the first direction X at a fixed pitch. Specifically, the first joined region row R1 is formed such that the inner joined region 22A1 and the outer joined region 22A2 are alternately arranged in one row along the first direction X at the fixed pitch. In the same manner, the plurality of second joined regions 22B form a second joined region row R2 where the second joined regions 22B are arranged in one row along the first direction X at a fixed pitch. The plurality of third joined regions 22C form a third joined region first row R31 where the third joined regions 22C are arranged in one row along the first direction X at a fixed pitch. The plurality of third joined regions 22C also form a third joined region second row R32 where the third joined regions 22C are arranged in one row along the first direction X at a fixed pitch, and are displaced from the third joined regions 22C of the third joined region first row R31 in the first direction X by a half pitch. The topsheet 2 includes, using the first joined region row R1 as the center, the second joined region row R2, the third joined region first row R31, the second joined region row R2, the third joined region second row R32, the second joined region row R2, the third joined region first row R31, and the second joined region row R2, these rows being arranged at fixed intervals in the second direction Y. These rows are arranged repeatedly in the second direction Y in this order.

As shown in FIG. 4, the pitch of the first joined regions 22A forming the first joined region row R1 is equal to the pitch in the first direction X of the second joined regions 22B forming the second joined region row R2. As shown in FIG. 4, the pitch in the first direction X of the third joined region 22C forming the third joined region first row R31 and the third joined region second row R32 is larger than the pitch in the first direction X of the first joined regions 22A forming the first joined region row R1.

The inner joined regions 22A1 of the first joined region 22A are formed at positions identical to positions of the third joined regions 22C of the third joined region first row R31 in the first direction X. The outer joined regions 22A2 are formed at positions identical to positions of the third joined regions 22C of the third joined region second row R32 in the first direction X. The second joined regions 22B of the second joined region row R2 disposed adjacently in the second direction Y are formed at positions identical to each other in the first direction X. Further, in spaces each of which is formed between two second joined regions 22B disposed adjacently in the first direction X, the third joined region 22C of the third joined region first row R31 and the third joined region 22C of the third joined region second row R32 are alternately positioned and formed in the first direction X.

Each projection 23 is formed in a region surrounded by the plurality of joined regions 22 formed as described above. Specifically, as shown in FIG. 4, when the topsheet 2 is viewed in a plan view, the first projection 23A is formed in a region surrounded by the outer joined regions 22A2 of the first joined regions 22A of the first joined region row R1, two adjacent second joined regions 22B and 22B of the second joined region row R2, two adjacent third joined regions 22C and 22C of the third joined region first row R31, two adjacent second joined regions 22B and 22B of the second joined region row R2, and the third joined region 22C of the third joined region second row R32. In the same manner, when the topsheet 2 is viewed in a plan view, the first projection 23A is formed in a region surrounded by the third joined region 22C of the third joined region first row R31, two adjacent second joined regions 22B and 22B of the second joined region row R2, two adjacent third joined regions 22C and 22C of the third joined region second row R32 and two adjacent second joined regions 22B and 22B of the second joined region row R2, and the third joined region 22C of the third joined region first row R31. Each first projection 23A is formed into an elliptical shape as viewed in a plan view. The major axis of the first projection 23A is aligned with the second direction Y, and the minor axis of the first projection 23A is aligned with the first direction X.

Further, when the topsheet 2 is viewed in a plan view, the second projection 23B is formed in a region surrounded by the inner joined region 22A1 of the first joined regions 22A of the first joined region row R1, two adjacent second joined regions 22B and 22B of the second joined region row R2, and the third joined region 22C of the third joined region first row R31. In the same manner, the second projection 23B is formed in a region surrounded by the second joined region 22B of the second joined region row R2, the inner joined region 22A1 and the outer joined region 22A2 which form the adjacent first joined regions 22A of the first joined region row R1, and the second joined region 22B of the second joined region row R2. The second projection 23B is formed into a circular shape as viewed in a plan view. The diameter of the second projection 23B is equal to the length of the minor axis of the first projection 23A. Accordingly, a region where the second projection 23B is formed is smaller than a region where the first projection 23A is formed.

When the topsheet 2 is viewed in a plan view, the first joined region 22A having the through hole 24, that is, the inner joined region 22A1, is positioned in the second projection region 23R which includes four second projections 23B surrounded by six first projections 23A arranged in an annular shape. In the diaper 1, the inner joined region 22A1 is positioned at the center of the four second projections 23B, that is, the center of the second projection region 23R. Further, the second projection region 23R is a region surrounded by the third joined region 22C of the third joined region first row R31, two adjacent second joined regions 22B and 22B of the second joined region row R2, two outer joined regions 22A2 and 22A2 disposed adjacently with the inner joined region 22A1 of the first joined region row R1 interposed therebetween, two adjacent second joined regions 22B and 22B of the second joined region row R2, and the third joined region 22C of the third joined region first row R31, the inner joined region 22A1 being positioned at the center of the region. With the provision of the second projection regions 23R having such a configuration, a body fluid is stored in the second projection regions 23R when a wearer urinates during wear of the diaper 1. Accordingly, even if the wearer urinates, the body fluid does not easily adhere to the wearer's skin so that dryness is enhanced. Further, the inner joined region 22A1 is provided in each second projection region 23R and hence, the body fluid stored in the second projection region 23R can be smoothly drawn into the absorbent member 4.

In the diaper 1, the topsheet 2 includes a plurality of second projection regions 23R, and the plurality of second projection regions 23R are arranged adjacently in the first direction X. In the diaper 1, the second projection regions 23R disposed adjacently in the first direction X are disposed adjacently with another first joined region 22A, that is, the outer joined region 22A2, interposed therebetween, another first joined region 22A being disposed adjacently to the inner joined region 22A1 disposed in one of the second projection regions 23R, and another first joined region 22A forming the first joined region row R1. The second projection regions 23R are arranged adjacently in the first direction X and hence, when a body fluid stored in the one second projection region 23R overflows, for example, the body fluid easily flows into another adjacent second projection region 23R. As described above, even if the body fluid overflows from the second projection region 23R, the body fluid flows into another second projection region 23R, and is drawn into the absorbent member 4 through another second projection region 23R. Accordingly, it is possible to suppress the lowering of fluid drawing performance.

In this description, "a second projection region 23R which includes the second projections 23B surrounded by the first projections 23A" means not only a state where the entire circumference of the second projection region 23R is completely surround but also a state where the second projection region 23R is substantially surrounded. The term "substantially surrounded" means a state where 60% or more of the entire circumference of the second projection region 23R is surround. In the diaper 1, 80% of the entire circumference of the second projection region 23R is surround by the six first projections 23A.

The first projection 23A and the second projection 23B have a shape which includes a top portion in cross section taken along either one of the first direction X or the second direction Y. As shown in FIG. 3 and FIG. 5, the first projections 23A and the second projections 23B are hollow. However, the shape of the first projections 23A and the second projections 23B is not limited to such a shape. Both projections 23A and 23B may not have a hollow structure, but may have a solid structure where the inside of both projections 23A and 23B is filled with a material for forming the topsheet 2.

Further, as shown in FIG. 5, a height H1 of the first projection 23A is larger than a height H2 of the second projection 23B (H1>H2). In this description, the height of the projection 23 (the first projection 23A or the second projection 23B) is the separation distance between the skin-facing surface of the first sheet 20 and the non-skin-facing surface of the second sheet 21 at a portion of the projection 23 where the first sheet 20 protrudes in a direction away from the second sheet 21. That is, the height of the projection 23 is an apparent thickness of the portion.

From the viewpoint of the storage capacity for a discharged body fluid, the ratio of the height H2 of the second projection 23B to the height H1 of the first projection 23A (H2/H1) is preferably set to 0.2 or more, and more preferably set to 0.3 or more. Further, the ratio is preferably set to 0.8 or less, and more preferably set to 0.7 or less. Specifically, the ratio is preferably set to 0.2 or more and 0.8 or less, and more preferably set to 0.3 or more and 0.7 or less.

From the same viewpoint, the height H1 of the first projection 23A is preferably set to 0.5 mm or more, and more preferably set to 0.7 mm or more. Further, the height H1 is preferably set to 5.0 mm or less, and more preferably set to 3.0 mm or less. Specifically, the height H1 is preferably set to 0.5 mm or more and 5.0 mm or less, and more preferably set to 0.7 mm or more and 3.0 mm or less.

From the same viewpoint, the height H2 of the second projection 23B is preferably set to 0.4 mm or more, and more preferably set to 0.5 mm or more. Further, the height H2 is preferably set to 3.0 mm or less, and more preferably set to 2.0 mm or less. Specifically, the height H2 is preferably set to 0.4 mm or more and 3.0 mm or less, and more preferably set to 0.5 mm or more and 2.0 mm or less.

The height H1 of the first projection 23A and the height H2 of the second projection 23B are measured as follows.

[Method for Measuring Height of Projection]

The cross section of a topsheet, which is a measure object, taken along a thickness direction of the topsheet is observed by a microscope to measure the height of a projection of the topsheet. More specifically, using a digital microscope VHX-1000 made by KEYENCE CORPORATION, the cross section is enlarged to a size at which projections and portions around the projections on the topsheet, which is the measurement object, sufficiently fall within the field, thus allowing the measurement of the projections (10 to 100 fold magnification). A measurement is performed on the height of the projection in the measurement field, that is, the height which corresponds to the height H1 of the projection 23 (the first projection 23A) shown in FIG. 5. That is, the measurement is performed on "the separation distance (the apparent thickness of the portion) between the skin-facing surface of the first sheet 20 and the non-skin-facing surface of the second sheet 21 at a portion of the projection 23 which protrudes in a direction along which the two sheets 20 and 21, which form the topsheet, are at the greatest separation from each other".

As shown in FIG. 5, the second projection regions 23R are provided to the skin-facing surface of the topsheet 2, each second projection region 23R including the plurality of second projections 23B surrounded by the plurality of first projections 23A having a larger height than the second projections 23B. With the provision of the second projection regions 23R, when a wearer urinates during wear of the diaper 1, the second projection regions 23R act as temporal storage portions for the body fluid. Accordingly, the body fluid does not easily adhere to wearer's skin so that dryness is enhanced. Further, the inner joined region 22A1, which is the first joined region 22A, is disposed in each second projection region 23R. Accordingly, for example, even in the case where a wearer discharges a large amount of body fluid, a body fluid can be smoothly drawn into the absorbent member 4 through the inner joined regions 22A1 so that dryness can be maintained by reducing stickiness, sweating and the like. Particularly, in the diaper 1, the inner joined region 22A1 is provided at the center of the four second projections 23B included in the second projection region 23R and hence, a body fluid can be efficiently drawn into the absorbent member 4.

Further, as shown in FIG. 5, the inner joined region 22A1 has the through hole 24 and hence, a body fluid can be drawn into the absorbent member 4 more smoothly. Further, each second projection region 23R is formed by surrounding the plurality of second projections 23B by the plurality of first projections 23A. Accordingly, it is possible to ensure a large area of the second projection region 23R.

A material for forming the topsheet 2 will be described. The first sheet 20 and the second sheet 21 which form the topsheet 2 are formed of sheet materials. As the sheet material, for example, a fiber sheet, such as a nonwoven fabric, a woven fabric and a knitted fabric, a film or the like may be used. From the viewpoint of skin-feel or the like, it is preferable to use a fiber sheet, and particularly preferable to use a nonwoven fabric. The same kind of sheet material may be used for forming the first sheet 20 and the second sheet 21, or different kinds of sheet materials may be used for forming the first sheet 20 and the second sheet 21. However, from the viewpoint of further increasing joining strength of the joined region 22 of both sheets 20 and 21, it is preferable to use the same kind of sheet.

A nonwoven fabric for forming both sheets 20 and 21 may be an air-through nonwoven fabric, a spun-bonded nonwoven fabric, a spunlace nonwoven fabric, a melt-blown nonwoven fabric, a resin-bonded nonwoven fabric, a needle punched nonwoven fabric or the like, for example. It is also possible to use a layered body obtained by combining two or more kinds of these nonwoven fabrics, or a layered body obtained by combining these nonwoven fabrics, a film and the like. Among these fabrics, it is preferable to use the air-through nonwoven fabric or the spun-bonded nonwoven fabric. Particularly, the first sheet 20 is a sheet positioned on the side which opposes the wearer's skin in a state where the wearer wears the diaper 1 and hence, the first sheet 20 is preferably formed of an air-through nonwoven fabric. The basis weight of the nonwoven fabric is preferably set to 10 $g/m^2$ or more, and more preferably set to 10 $g/m^2$ or more. The basis weight of the nonwoven fabric is preferably set to 100 $g/m^2$ or less, and more preferably set to 30 $g/m^2$ or less.

For a constituent fiber of a nonwoven fabric which forms both sheets 20 and 21, a fiber (fusion bondable fiber) made of various thermoplastic resins may be used. The thermoplastic resins may be polyolefin, such as polyethylene or polypropylene; polyester, such as polyethylene terephthalate; polyamide, such as nylon 6 or nylon 66; polyacrylic acid, polymethacrylic acid alkyl ester, polyvinyl chloride, polyvinylidene chloride and the like. One kind of these resins may be used in a single form, or two or more kinds of these resins may be used in combination. The fusion bondable fiber may be either a short fiber or a long fiber, and may be either a hydrophilic fiber or a water-repellent fiber. Further, a sheath-core type or side-by-side type composite fiber, a split fiber, a modified cross-section fiber, a heat shrinkable fiber or the like may also be used. One kind of these fibers may be used in a single form, or two or more kinds of these fibers may be used in combination. Further, both sheets 20 and 21 may be or may not be equal to each other in composition. In this embodiment, "equal to each other in composition" means that both sheets 20 and 21 have the same forming materials and the same content of these materials. However, appearance factors, such as sizes, shapes as viewed in a plan view of respective portions, may be or may not be equal to each other.

A preferred example of a nonwoven fabric for forming both sheets 20 and 21 may be a nonwoven fabric which includes, as constituent fibers, one, two or more kinds of fusion bondable composite fiber formed of two or more kinds of resins. Such a nonwoven fabric may be a nonwoven fabric which includes two kinds of sheath-core type fusion bondable composite fibers, for example. A point which makes two kinds of sheath-core type fusion bondable composite fibers different from each other is preferably 1) a point that the kind of resin for a sheath component differs, or 2) a point that a volume ratio between a resin for a core component and a resin for a sheath component differs with the same kind of resin for the core component and the same kind of resin for the sheath component.

Further, it is preferable that the topsheet 2 has a large number of intersection points between fusion bondable composite fibers (preferably sheath-core type fusion bondable composite fibers), which are constituent fibers, and the fusion bondable composite fibers are fusion bonded at least at some of the large number of intersection points. With the formation of the large number of such fusion bonding points between the fusion bondable composite fibers on the topsheet 2, various characteristics of the topsheet 2, such as softness, can be controlled through a control of the number of such fusion bonding points and a fusion-bonding strength between fibers at the fusion bonding points. Accordingly, the characteristics of the topsheet 2, such as softness, can be further enhanced.

From the viewpoint of causing the topsheet 2 to have a large number of fusion bonding points between the fusion bondable composite fibers as described above, it is preferable that the topsheet 2 includes two or more kinds of fusion bondable composite fibers as constituent fibers. There may be a case where the first sheet 20 and the second sheet 21 which form the topsheet 2 are formed of nonwoven fabrics obtained such that hot air treatment by an air-through method or the like is applied to webs obtained from a carding machine to cause intersection points between the constituent fibers to be fusion bonded by such hot air treatment. Particularly in such a case, when two or more kinds of fusion bondable composite fibers are used as the constituent fibers for both sheets 20 and 21, ease of fusion bonding between the constituent fibers varies depending on a combination of the constituent fibers. Accordingly, it is possible to more easily control the number of fusion bonding points between the constituent fibers (fusion bondable composite fibers) and a fusion-bonding strength between the fibers at the fusion bonding points and hence, softness of the topsheet 2 may be further enhanced. The fusion bondable composite fiber (preferably sheath-core type fusion bondable composite fiber) may be included in either one or both of both sheets 20 and 21, which form the topsheet 2. It is preferable that the fusion bondable composite fiber is included at least in the first sheet 20 which is positioned on the side relatively close to the wearer's skin, thus being required to have softness.

It is preferable that both sheets 20 and 21 include, as a fusion bondable fiber, a latently crimpable fusion bondable fiber where crimping is realized. The latently crimpable fusion bondable fiber may be an eccentric sheath-core type composite fiber, a side-by-side type composite fiber or the like which contains two kinds of thermoplastic polymer materials having different shrinkage rates as components, for example. A preferred example of two kinds of thermoplastic polymer materials having different shrinkage rates may be a combination of ethylene-propylene random copolymer (EP) and polypropylene (PP), for example. As described above, the region where the second projection 23B is formed is smaller than the region where the first projection 23A is formed. Therefore, due to the realization of crimping of the fusion bondable fiber, the first projections 23A rise more easily than the second projections 23B. Accordingly, in the topsheet 2 of the diaper 1, as shown in FIG. 5, the first projections 23A are formed with a height larger than the height of the second projections 23B.

The topsheet 2 having the above-mentioned configuration may be manufactured according to a method for manufacturing a composite sheet disclosed in Japanese Patent Laid-Open No. 2015-112343, for example. Specifically, the topsheet 2 can be acquired as follows. For example, a continuous first sheet 20 is supplied between a first roller and a second roller, where peripheral surfaces of the first roller and the second roller have shapes which can be engaged with each other, to cause the first sheet 20 to be deformed into uneven shapes. Then, the first sheet 20 is moved from the engagement portion along the peripheral surface portion of the first roller and, thereafter, the second sheet 21 is supplied to overlap with the first sheet 20. Then, both sheets 20 and 21 are clamped while being heated between projections of the first roller and a heat roller so that both sheets 20 and 21 are partially joined. At this point of operation, uneven shapes of the first roller and the second roller, and a pattern of the joined region formed by the first roller and the heat roller are made different between the center portion of the first sheet 20 and sides of the first sheet 20. When the first sheet 20 is deformed into an uneven shape by causing the first sheet 20 to be bitten by the engagement portion between the first roller and the second roller, it is preferable that the deformation of the first sheet 20 into the uneven shape is promoted by suctioning the first sheet 20 to the inner side of the roller.

Figure 6:
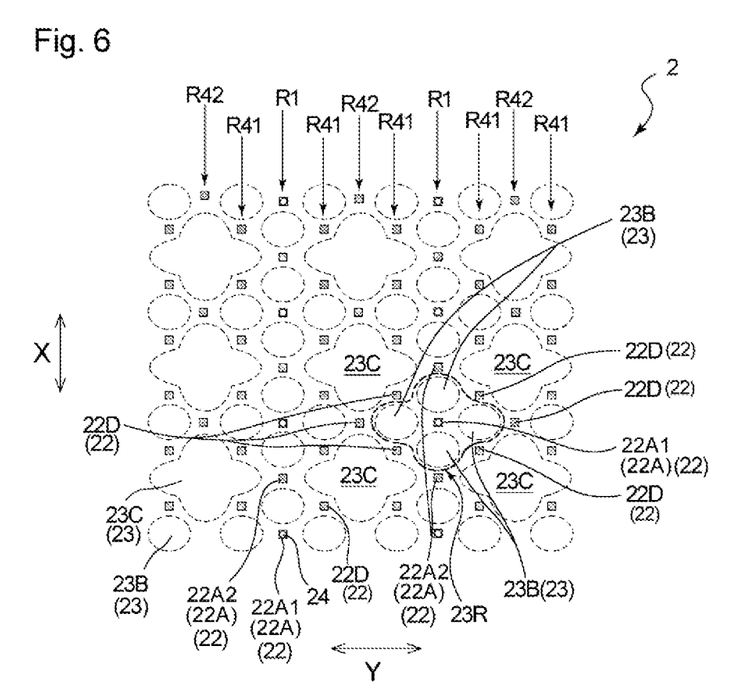
FIG. 6 is a plan view (a view which corresponds to FIG. 4) schematically showing a portion on the skin-facing surface side of a topsheet of the absorbent article of another embodiment of the present invention.

FIG. 6 shows a portion of the topsheet 2 of another embodiment on the skin-facing surface side in an enlarged manner. With respect to the topsheet 2 shown in FIG. 6, components which are different from those of the topsheet 2 shown in FIG. 4 are mainly described, similar components are given the same reference numerals, and the description of such components is omitted. With respect to components of the topsheet 2 which are not described, the description of the topsheet 2 shown in FIG. 3 to FIG. 5 is appropriately applied.

The topsheet 2 shown in FIG. 6 includes, as the plurality of joined regions 22, the plurality of first joined regions 22A and a plurality of fourth joined regions 22D. In the fourth joined region 22D, the first sheet 20 and the second sheet 21 are pressed into an integral body by embossing so that the fourth joined region 22D has a higher density than other portions where embossing is not performed. It is preferable that both sheets 20 and 21 are fusion bonded by melting of a configuration resin for one of or both sheets 20 and 21 and by subsequent solidification of the configuration resin.

As shown in FIG. 6, the fourth joined region 22D is formed into a square shape as viewed in a plan view, and each side of the fourth joined region 22D is aligned with the first direction X or the second direction Y. The plurality of fourth joined regions 22D form a fourth joined region first row R41 where the fourth joined regions 22D are arranged in one row along the first direction X at a fixed pitch. The plurality of fourth joined regions 22D also form a fourth joined region second row R42 where the fourth joined regions 22D are arranged in one row along the first direction X at a pitch larger than the pitch of the fourth joined regions 22D forming the fourth joined region first row R41. The topsheet 2 shown in FIG. 6 includes, using the first joined region row R1 as the center, the fourth joined region first row R41, the fourth joined region second row R42, and the fourth joined region first row R41 which are arranged at fixed intervals in the second direction Y. These rows are arranged repeatedly in the second direction Y in this order.

As shown in FIG. 6, the pitch in the first direction X of the fourth joined regions 22D forming the fourth joined region first row R41 is equal to the pitch in the first direction X of the first joined regions 22A forming the first joined region row R1. Further, the pitch in the first direction X of the fourth joined regions 22D forming the fourth joined region second row R42 is larger than the pitch in the first direction X of the first joined regions 22A forming the first joined region row R1.

The fourth joined regions 22D of the fourth joined region first rows R41 disposed adjacently in the second direction Y are formed at positions identical to each other in the first direction X. Further, between the fourth joined regions 22D of the fourth joined region first row R41 disposed adjacently in the first direction X, the outer joined region 22A2 of the first joined regions 22A forming the first joined region row R1 is positioned and formed. Further, the fourth joined region 22D forming the fourth joined region second row R42 is formed at a position identical to the position of the inner joined region 22A1 of the first joined regions 22A forming the first joined region row R1 in the first direction X.

The respective projections 23 are formed in a region surrounded by the plurality of joined regions 22 formed as described above. Specifically, as shown in FIG. 6, when the topsheet 2 is viewed in a plan view, a third projections 23C is formed in a region surrounded by the outer joined region 22A2 of the first joined region row R1, two adjacent fourth joined regions 22D and 22D of the fourth joined region first row R41, two adjacent fourth joined regions 22D and 22D of the fourth joined region second row R42, two adjacent fourth joined regions 22D and 22D of the fourth joined region first row R41, and the outer joined region 22A2 of the first joined region row R1. As viewed in a plan view, the third projection 23C has a substantially cross shape where third projection 23C extends in four directions from the center portion, and extending directions are aligned with the first direction X or the second direction Y.

Further, when the topsheet 2 shown in FIG. 6 is viewed in a plan view, the second projection 23B is formed in a region surrounded by the inner joined region 22A1 of the first joined region row R1, two adjacent fourth joined regions 22D and 22D of the fourth joined region first row R41, and the fourth joined region 22D of the fourth joined region second row R42. In the same manner, the second projection 23B is formed in a region surrounded by the fourth joined region 22D of the fourth joined region first row R41, the inner joined region 22A1 and the outer joined region 22A2 which form the adjacent first joined regions 22A of the first joined region row R1, and the fourth joined region 22D of the fourth joined region first row R41.

When the topsheet 2 shown in FIG. 6 is viewed in a plan view, the second projection region 23R is formed which includes four second projections 23B surrounded by four third projections 23C arranged in an annular shape. The inner joined region 22A1 having the through hole 24, which is the third joined region 22C, is positioned in the second projection region 23R. Further, the second projection region 23R is also a region surrounded by the fourth joined region 22D of the fourth joined region second row R42, two adjacent fourth joined regions 22D and 22D of the fourth joined region first row R41, two outer joined regions 22A2 and 22A2 disposed adjacently with the inner joined region 22A1 of the first joined region row R1 interposed therebetween, two adjacent fourth joined regions 22D and 22D of the fourth joined region first row R41, and the fourth joined region 22D of the fourth joined region second row R42, the inner joined region 22A1 being positioned at the center of the region. The diaper 1 which includes the topsheet 2 shown in FIG. 6 can also acquire the advantageous effects substantially equal to those of the diaper 1 which includes the topsheet 2 shown in FIG. 4.

Figure 7:
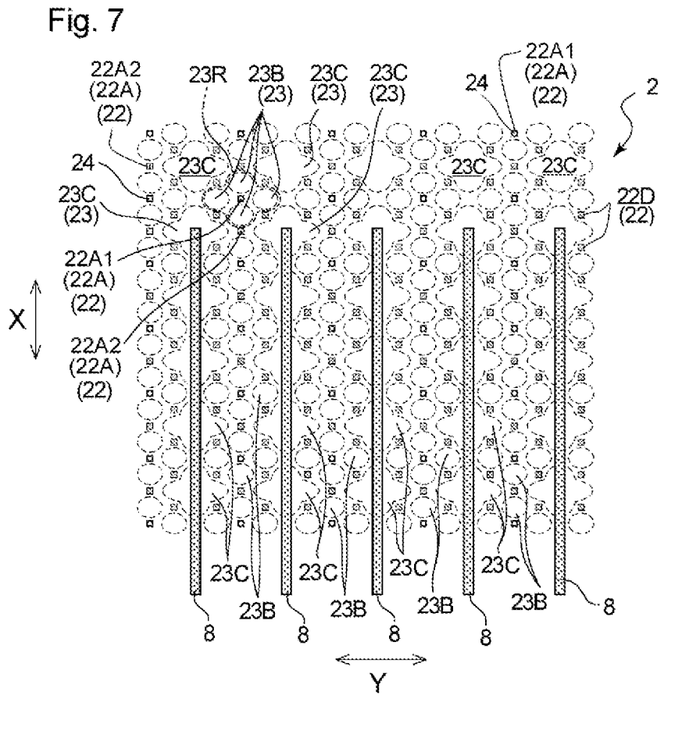
FIG. 7 is a plan view showing a coating pattern of an adhesive applied to the topsheet of the absorbent article of the present invention.

In fixing the topsheet 2 and the absorbent member 4 by a hot melt adhesive 8, it is preferable that a larger amount of the hot melt adhesive 8 is applied to portions of the non-skin-facing surface of the topsheet 2 which correspond to a region including the first projections 23A (see FIG. 4) or the third projections 23C (see FIG. 7) which surround the second projection regions 23R than to the portions of the non-skin-facing surface of the topsheet 2 which correspond to the second projection regions 23R of the topsheet 2. From the viewpoint of suppressing the inhibition of absorption of a body fluid into the absorbent member 4, in the topsheet 2 shown in FIG. 4, it is preferable that the hot melt adhesive 8 is stretched in the first direction X on the non-skin-facing surface corresponding to the region including the center of the third projections 23C as shown in FIG. 7, for example, thus forming a stripe shape where the hot melt adhesives 8 are arranged intermittently in the second direction Y.

Figure 8:
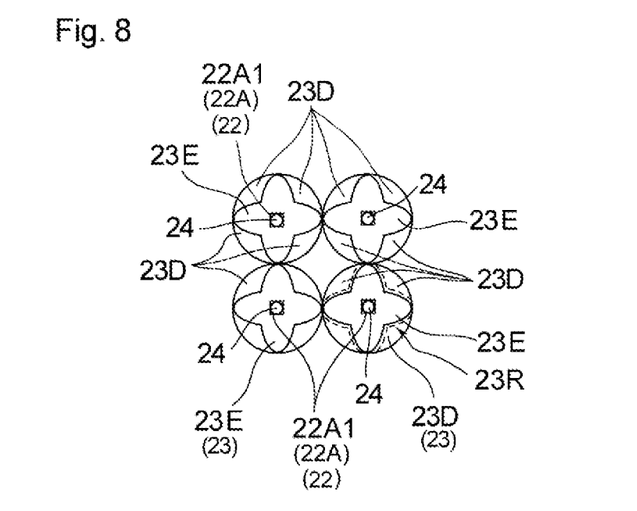
FIG. 8 is a plan view schematically showing a portion on the skin-facing surface side of a topsheet of the absorbent article of another embodiment of the present invention.

The present invention has been described heretofore based on the preferred embodiment of the present invention. However, the present invention is not limited to the above-mentioned embodiment. For example, in the topsheet 2 shown in FIG. 4 and FIG. 6, the second projection region 23R is formed by including the plurality of second projections 23B surrounded by the plurality of first projections 23A or the third projections 23C. However, the second projection region 23R may be formed by including only one second projection 23B. For example, the second projection region 23R may be formed by including only one second projection 23E surrounded by four first projections 23D as shown in FIG. 8.

Further, in the topsheet 2 shown in FIG. 4 and FIG. 6, the inner joined region 22A1 is disposed at the center of the second projection region 23R. However, provided that the inner joined region 22A1 is disposed in the second projection region 23R, the inner joined region 22A1 may be disposed at a portion of the second projection region 23R other than the center of the second projection region 23R.

Related to the above-mentioned embodiment, the present invention further discloses the following absorbent article.

<1>
An absorbent article comprising: an absorbent member; and a topsheet disposed on a skin-facing surface side of the absorbent member, the absorbent article having a longitudinal direction, which corresponds to a front-rear direction of a wearer, and a lateral direction orthogonal to the longitudinal direction, wherein the topsheet comprises a layered body formed of a first sheet, disposed on a wearer's skin side, and a second sheet, disposed on a non-skin side, the first sheet and the second sheet of the layered body are partially joined to form a plurality of joined regions, and the first sheet comprises a plurality of projections, which protrude from the second sheet toward the wearer's skin side, at a portion other than the joined regions, the projections comprise a first projection and a second projection, and a height of the first projection is larger than a height of the second projection, when the topsheet is viewed in a plan view, a second projection region is formed which comprises the second projection surrounded by a plurality of the first projections, and when the topsheet is viewed in a plan view, the joined regions comprise an inner joined region in the second projection region.

<2>
The absorbent article as set forth in clause <1>, wherein the second projection region is formed by comprising a plurality of the second projections.

<3>
The absorbent article as set forth in clause <1> or <2>, wherein the absorbent article comprises a plurality of the second projection regions, and the plurality of the second projection regions are arranged adjacently in at least one of the longitudinal direction and the lateral direction.

<4>
The absorbent article as set forth in any one of clauses <1> to <3>, wherein the topsheet and the absorbent member are fixed with each other by an adhesive, and a larger amount of the adhesive is applied to a portion of the topsheet which corresponds to a region comprising the first projections, which surround the second projections in the second projection region, than to a portion of the topsheet which corresponds to the second projection region of the topsheet.

<5>
The absorbent article as set forth in any one of clauses <1> to <4>, wherein the inner joined region has a through hole which penetrates the first sheet and the second sheet.

<6>
The absorbent article as set forth in any one of clauses <1> to <5>, wherein the absorbent article comprises a front portion disposed on a front side of the wearer during wear, a rear portion disposed on a rear side of the wearer during wear, and a crotch portion positioned between the front portion and the rear portion during wear, and the plurality of the projections are disposed in an entire region from the front portion to the rear portion.

<7>
The absorbent article as set forth in any one of clauses <1> to <6>, wherein the topsheet comprises the plurality of the joined regions formed in a state of being regularly distributed in a plane direction of the topsheet.

<8>
The absorbent article as set forth in any one of clauses <1> to <7>, wherein, in the joined region, the first sheet and the second sheet are pressed into an integral body by embossing so that the joined region has a higher density than other portions.

<9>
The absorbent article as set forth in any one of clauses <1> to <8>, wherein the first sheet and the second sheet are fusion bonded by melting of a configuration resin for one or both of the first sheet and the second sheet and by subsequent solidification of the configuration resin.

<10>
The absorbent article as set forth in any one of clauses <1> to <9>, wherein the plurality of the joined regions comprise first joined regions, and the first joined regions comprise an inner joined region disposed in the second projection region, and an outer joined region disposed outside the second projection region, and each of the inner joined region and the outer joined region is formed of one joined portion having a square shape as viewed in a plan view, and each side of the inner joined region and each side of the outer joined region are aligned with a first direction or a second direction.

<11>
The absorbent article as set forth in clause <10>, wherein the inner joined region has a through hole which penetrates the first sheet and the second sheet.

<12>
The absorbent article as set forth in clause <10> or <11>, wherein the plurality of the joined regions comprise second joined regions each of which is formed of two second joined portions each of which is formed into a square shape as viewed in a plan view, and an outer shape of each of the second joined portions as viewed in a plan view is formed into a square shape as viewed in a plan view, the square shape having a shape and size identical to a shape and size of the first joined region, and each side of the second joined portion is aligned with the first direction or the second direction.

<13>
The absorbent article as set forth in clause <12>, wherein the plurality of the joined regions comprise third joined regions each of which is formed of one joined portion having a rectangular shape as viewed in a plan view, a longitudinal direction of the third joined region is aligned with the first direction, and a short direction of the third joined region is aligned with the second direction.

<14>
The absorbent article as set forth in clause <13>, wherein the first joined regions form a first joined region row where the inner joined region and the outer joined region are alternately arranged in one row along the first direction at a fixed pitch, a plurality of the second joined regions form a second joined region row where the second joined regions are arranged in one row along the first direction at a fixed pitch, a plurality of the third joined regions form a third joined region first row where the third joined regions are arranged in one row along the first direction at a fixed pitch, and the plurality of the third joined regions form a third joined region second row where the third joined regions are displaced from the third joined region first row in the first direction by a half pitch, and the topsheet comprises, using the first joined region row as a center, the second joined region row, the third joined region first row, the second joined region row, the third joined region second row, the second joined region row, the third joined region first row, and the second joined region row which are arranged at fixed intervals in the second direction, and which are arranged repeatedly in the second direction in this order.
<15>
The absorbent article as set forth in clause <14>, wherein a pitch of the first joined regions forming the first joined region row is equal to a pitch in the first direction of the second joined regions forming the second joined region row.
<16>
The absorbent article as set forth in clause <14> or <15>, wherein a pitch in the first direction of the third joined regions forming the third joined region first row and the third joined region second row is larger than the pitch in the first direction of the first joined regions forming the first joined region row.
<17>
The absorbent article as set forth in any one of clauses <14> to <16>, wherein the inner joined region of the first joined region is formed at a position identical to a position of the third joined region of the third joined region first row in the first direction, and the outer joined region is formed at a position identical to a position of the third joined region of the third joined region second row in the first direction.
<18>
The absorbent article as set forth in any one of clauses <14> to <17>, wherein the second joined regions of the second joined region rows disposed adjacently in the second direction are formed at positions identical to each other in the first direction.
<19>
The absorbent article as set forth in any one of clauses <14> to <18>, wherein in spaces each of which is formed between the second joined regions disposed adjacently in the first direction, the third joined region of the third joined region first row and the third joined region of the third joined region second row are alternately positioned and formed in the first direction.
<20>
The absorbent article as set forth in any one of clauses <1> to <19>, wherein the first projection is formed into an elliptical shape as viewed in a plan view, a major axis of the first projection is aligned with the second direction, and a minor axis of the first projection is aligned with the first direction.
<21>
The absorbent article as set forth in any one of clauses <1> to <20>, wherein the second projection is formed into a circular shape as viewed in a plan view, and a diameter of the second projection is equal to a length of the minor axis of the first projection.
<22>
The absorbent article as set forth in any one of clauses <1> to <21>, wherein the second projection region is formed, which comprises four second projections surrounded by six first projections arranged in an annular shape when the topsheet is viewed in a plan view.
<23>
The absorbent article as set forth in any one of clauses <1> to <22>, wherein the plurality of the joined regions comprise the inner joined region which has the through hole, and the inner joined region is positioned at a center of the four second projections, that is, a center of the second projection region.
<24>
The absorbent article as set forth in any one of clauses <14> to <19>, wherein the second projection regions disposed adjacently in the first direction are disposed adjacently with the outer joined region interposed between the second projection regions, the outer joined region being disposed adjacently to the inner joined region disposed in one of the second projection regions, and the outer joined region being another first joined region which forms the first joined region row.
<25>
The absorbent article as set forth in any one of clauses <1> to <24>, wherein the first projection and the second projection are hollow.
<26>
The absorbent article as set forth in any one of clauses <1> to <25>, wherein a ratio of a height H2 of the second projection to a height H1 of the first projection (H2/H1) is preferably set to 0.2 or more, and more preferably set to 0.3 or more and, further, the ratio is preferably set to 0.8 or less, and more preferably set to 0.7 or less.
<27>
The absorbent article as set forth in any one of clauses <1> to <26>, wherein the height H1 of the first projections is preferably set to 0.5 mm or more, and more preferably set to 0.7 mm or more and, further, the height H1 is preferably set to 5.0 mm or less, and more preferably set to 3.0 mm or less.
<28>
The absorbent article as set forth in any one of clauses <1> to <27>, wherein the height H2 of the second projections is preferably set to 0.4 mm or more, and more preferably set to 0.5 mm or more and, further, the height H2 is preferably set to 3.0 mm or less, and more preferably set to 2.0 mm or less.
<29>
The absorbent article as set forth in any one of clauses <1> to <11>, wherein the plurality of the joined regions comprise fourth joined regions formed into a square shape as viewed in a plan view, each side of the fourth joined region being aligned with the first direction or the second direction, and a plurality of the fourth joined regions form a fourth joined region first row where the fourth joined regions are arranged in one row along the first direction at a fixed pitch, and the plurality of the fourth joined regions form a fourth joined region second row where the fourth joined regions are arranged in one row along the first direction at a pitch larger than a pitch of the fourth joined regions forming the fourth joined region first row.
<30>
The absorbent article as set forth in clause <29>, wherein the plurality of the joined regions comprise first joined regions, and the first joined regions comprise an inner joined region disposed in the second projection region, and an outer joined region disposed outside the second projection region, the inner joined region and the outer joined region are alternately arranged in one row along the first direction at a fixed pitch, thus forming a first joined region row, and the topsheet comprises, using the first joined region row as a center, the fourth joined region first row, the fourth joined region second row, and the fourth joined region first row which are arranged at fixed intervals in the second direction, and which are arranged repeatedly in the second direction in this order.

<31>

The absorbent article as set forth in clause <30>, wherein a pitch in the first direction of the fourth joined regions forming the fourth joined region first row is equal to a pitch in the first direction of the first joined regions forming the first joined region row.

<32>

The absorbent article as set forth in clause <30> or <31>, wherein a pitch in the first direction of the fourth joined regions forming the fourth joined region second row is larger than the pitch in the first direction of the first joined regions forming the first joined region row.

<33>

The absorbent article as set forth in any one of clauses <30> to <32>, wherein the fourth joined regions of the fourth joined region first rows disposed adjacently in the second direction are formed at positions identical to each other in the first direction.

<34>

The absorbent article as set forth in any one of clauses <30> to <33>, wherein between the fourth joined regions of the fourth joined region first row, the fourth joined regions being disposed adjacently in the first direction, the outer joined region of the first joined regions forming the first joined region row is positioned and formed.

<35>

The absorbent article as set forth in any one of clauses <30> to <34>, wherein the fourth joined region forming the fourth joined region second row is formed at a position identical to a position of the inner joined region of the first joined regions forming the first joined region row in the first direction.

INDUSTRIAL APPLICABILITY

According to the absorbent article of the present invention, even in the case where a large amount of body fluid is discharged, a body fluid is smoothly transferred from the topsheet to the absorbent member so that dryness can be enhanced by reducing stickiness and sweating.

The invention claimed is:

1. An absorbent article comprising: an absorbent member; and a topsheet disposed on a skin-facing surface side of the absorbent member, the absorbent article having a longitudinal direction, which corresponds to a front-rear direction of a wearer, and a lateral direction orthogonal to the longitudinal direction, wherein
the topsheet comprises a layered body formed of a first sheet, disposed on the skin-facing surface side, and a second sheet, disposed on a non-skin-facing surface side, the first sheet and the second sheet of the layered body are partially joined to form a plurality of joined regions, and the first sheet forms a plurality of projections, which protrude from the second sheet toward a wearer's skin side, at a portion other than the joined regions,
the projections comprise a first projection and a second projection, and a height of the first projection is longer than a height of the second projection,
when the topsheet is viewed in a plan view, a second projection region which comprises the second projection surrounded by a plurality of the first projections is formed, and
when the topsheet is viewed in a plan view, the joined regions comprise an inner joined region in the second projection region, wherein
the plurality of the joined regions comprise first joined regions, and the first joined regions comprise the inner joined region disposed in the second projection region, and an outer joined region disposed outside the second projection region, and
each of the inner joined region and the outer joined region is formed of one joined portion having a square shape as viewed in a plan view, and each side of the inner joined region and each side of the outer joined region are aligned with a first direction or a second direction, wherein
the plurality of the joined regions comprise second joined regions each of which is formed of two second joined portions, and
an outer shape of each of the second joined portions as viewed in a plan view is formed into a square shape, the square shape having a shape and size identical to a shape and size of the first joined regions, and each side of the second joined portions is aligned with the first direction or the second direction, wherein
the plurality of the joined regions comprise third joined regions each of which is formed of one joined portion having a rectangular shape as viewed in a plan view, a longitudinal direction of each of the third joined regions is aligned with the first direction, and a short direction of each of the third joined regions is aligned with the second direction, and
the first joined regions form a first joined region row where the inner joined region and the outer joined region are alternately arranged in one row along the first direction at a fixed pitch,
a plurality of the second joined regions form a second joined region row where the second joined regions are arranged in one row along the first direction at a fixed pitch,
a plurality of the third joined regions form a third joined region first row where the third joined regions are arranged in one row along the first direction at a fixed pitch, and the plurality of the third joined regions form a third joined region second row where the third joined regions are displaced from the third joined region first row in the first direction by a half pitch, and
the topsheet comprises, using the first joined region row as a center, the second joined region row, the third joined region first row, the second joined region row, the third joined region second row, the second joined region row, the third joined region first row, and the second joined region row which are arranged at fixed intervals in the second direction, and which are arranged repeatedly in the second direction in this order.

2. The absorbent article according to claim 1, wherein the second projection region comprises a plurality of the second projections.

3. The absorbent article according to claim 1, wherein the absorbent article comprises a plurality of the second projection regions, and the plurality of the second projection regions are arranged adjacently in at least one of the longitudinal direction and the lateral direction.

4. The absorbent article according to claim 3, wherein second projection regions are disposed adjacently in the first direction and are disposed adjacently with the outer joined region interposed between the second projection regions, the outer joined region being disposed adjacently to the inner joined region disposed in one of the second projection regions, and the outer joined region being another first joined region which forms the first joined region row.

5. The absorbent article according to claim 1, wherein
the topsheet and the absorbent member are fixed with each other by an adhesive, and
a larger amount of the adhesive is applied to a portion of the topsheet which corresponds to a region comprising the first projections, which surround the second projection in the second projection region, than to a portion of the topsheet which corresponds to the second projection region of the topsheet.

6. The absorbent article according to claim 1, wherein
the inner joined region has a through hole which penetrates the first sheet and the second sheet.

7. The absorbent article according to claim 1, wherein the pitch of the first joined regions forming the first joined region row is equal to the pitch in the first direction of the second joined regions forming the second joined region row.

8. The absorbent article according to claim 1, wherein the pitch in the first direction of the third joined regions forming the third joined region first row and the third joined region second row is larger than the pitch in the first direction of the first joined regions forming the first joined region row.

9. The absorbent article according to claim 1, wherein the inner joined region of the first joined region is formed at a position identical to a position of a third joined region of a third joined region first row in the first direction, and the outer joined region is formed at a position identical to a position of a third joined region of a third joined region second row in the first direction.

10. The absorbent article according to claim 1, wherein the second joined regions of each of the second joined region rows are disposed adjacently in the second direction and are formed at positions identical to each other in the first direction.

11. The absorbent article according to claim 1, wherein, in spaces formed between the second joined regions, which are disposed adjacently in the first direction, a third joined region of a third joined region first row and a third joined region of a third joined region second row are alternately positioned and formed in the first direction.

12. The absorbent article according to claim 1, wherein the first projection is formed into an elliptical shape as viewed in a plan view, a major axis of the first projection is aligned with the second direction, and a minor axis of the first projection is aligned with the first direction.

13. The absorbent article according to claim 12, wherein the second projection is formed into a circular shape as viewed in a plan view, and a diameter of the second projection is equal to a length of the minor axis of the first projection.

14. The absorbent article according to claim 1, wherein the second projection region is formed, which comprises four second projections surrounded by six first projections arranged in an annular shape when the topsheet is viewed in a plan view.

15. The absorbent article according to claim 14, wherein the plurality of the joined regions comprise the inner joined region which has a through hole, and the inner joined region is positioned at a center of the four second projections, that is, a center of the second projection region.

16. The absorbent article according to claim 1, wherein the first projection and the second projection are hollow.

* * * * *